United States Patent
Masel

(10) Patent No.: US 10,280,378 B2
(45) Date of Patent: May 7, 2019

(54) SYSTEM AND PROCESS FOR THE PRODUCTION OF RENEWABLE FUELS AND CHEMICALS

(71) Applicant: Dioxide Materials, Inc., Boca Raton, FL (US)

(72) Inventor: Richard I. Masel, Boca Raton, FL (US)

(73) Assignee: Dioxide Materials, Inc, Boca Raton, FL (US)

( * ) Notice: Subject to any disclaimer, the term of this patent is extended or adjusted under 35 U.S.C. 154(b) by 0 days.

(21) Appl. No.: 15/684,548

(22) Filed: Aug. 23, 2017

(65) Prior Publication Data

US 2018/0127668 A1 May 10, 2018

Related U.S. Application Data

(63) Continuation-in-part of application No. 15/158,227, filed on May 18, 2016, which is a continuation-in-part
(Continued)

(51) Int. Cl.
*C25B 1/00* (2006.01)
*C10L 1/06* (2006.01)
(Continued)

(52) U.S. Cl.
CPC .............. *C10L 1/06* (2013.01); *B01J 19/245* (2013.01); *B01J 21/04* (2013.01); *B01J 23/755* (2013.01);
(Continued)

(58) Field of Classification Search
CPC .... C25B 1/00; C25B 1/04; C25B 9/18; C10L 2290/38
See application file for complete search history.

(56) References Cited

U.S. PATENT DOCUMENTS 2,996,359 A 8/1961 Mossman et al.
3,779,883 A 12/1973 Heit
(Continued)

FOREIGN PATENT DOCUMENTS

JP H02166128 4/2016
KR 101360269 B1 2/2014
(Continued)

OTHER PUBLICATIONS

Li et al., "Novel anion exchange membranes based on polymerizable imidazolium salt for alkaline fuel cell applications", J. Mater. Chem. 21 (2011), pp. 11340-11346.*
(Continued)

*Primary Examiner* — Mark S Kaucher
(74) *Attorney, Agent, or Firm* — Corridor Law Group, P.C.

(57) ABSTRACT

A renewable fuel production system includes a carbon dioxide capture unit for extracting carbon dioxide from atmospheric air, a carbon dioxide electrolyzer for converting carbon dioxide to carbon monoxide, a water electrolyzer for converting water to hydrogen, a synfuels generator for converting carbon monoxide produced by the carbon dioxide electrolyzer and hydrogen produced by the water electrolyzer to a fuel. The fuel produced can be synthetic gasoline and/or synthetic diesel. A renewable fuel production process includes the steps of extracting carbon dioxide from atmospheric air via a carbon dioxide capture unit, converting carbon dioxide to carbon monoxide via a carbon dioxide electrolyzer, converting water to hydrogen via a water electrolyzer, and converting carbon monoxide produced via the carbon dioxide electrolyzer and $H_2$ produced via the water electrolyzer to a fuel. The system is also capable of simultaneously or alternatively producing a separate industrial chemical.

12 Claims, 4 Drawing Sheets

Related U.S. Application Data of application No. 14/704,935, filed on May 5, 2015, now Pat. No. 9,370,773, application No. 15/684,548, which is a continuation-in-part of application No. 15/400,775, filed on Jan. 6, 2017, now Pat. No. 9,849,450, which is a continuation-in-part of application No. 15/090,477, filed on Apr. 4, 2016, now Pat. No. 9,580,824.

(51) Int. Cl.

| | |
|---|---|
| C25B 1/04 | (2006.01) |
| C25B 11/04 | (2006.01) |
| C25B 13/08 | (2006.01) |
| C10L 1/08 | (2006.01) |
| C07C 1/22 | (2006.01) |
| C07C 29/154 | (2006.01) |
| C07C 41/09 | (2006.01) |
| B01J 19/24 | (2006.01) |
| B01J 29/06 | (2006.01) |
| B01J 35/10 | (2006.01) |
| C25B 9/18 | (2006.01) |
| C07C 29/151 | (2006.01) |
| B01J 35/00 | (2006.01) |
| B01J 21/04 | (2006.01) |
| B01J 23/755 | (2006.01) |
| B01J 23/80 | (2006.01) |
| B01J 23/882 | (2006.01) |
| B01J 29/40 | (2006.01) |
| B01J 29/85 | (2006.01) |

(52) U.S. Cl.
CPC ............ *B01J 23/80* (2013.01); *B01J 23/882* (2013.01); *B01J 29/06* (2013.01); *B01J 29/40* (2013.01); *B01J 29/85* (2013.01); *B01J 35/0006* (2013.01); *B01J 35/1019* (2013.01); *C07C 1/22* (2013.01); *C07C 29/154* (2013.01); *C07C 29/1518* (2013.01); *C07C 41/09* (2013.01); *C10L 1/08* (2013.01); *C25B 1/00* (2013.01); *C25B 1/04* (2013.01); *C25B 9/18* (2013.01); *C25B 11/0478* (2013.01); *C25B 13/08* (2013.01); *C10L 2200/0423* (2013.01); *C10L 2200/0446* (2013.01); *C10L 2270/023* (2013.01); *C10L 2270/026* (2013.01); *C10L 2290/38* (2013.01); *Y02E 60/366* (2013.01); *Y02E 70/10* (2013.01); *Y02P 20/52* (2015.11)

(56) References Cited

U.S. PATENT DOCUMENTS

| | | | |
|---|---|---|---|
| 3,896,015 | A | 7/1975 | McRae |
| 4,113,922 | A | 9/1978 | DAgostino et al. |
| 4,430,445 | A | 2/1984 | Miyake et al. |
| 4,456,521 | A | 6/1984 | Solomon et al. |
| 4,921,585 | A | 5/1990 | Molter |
| 4,968,393 | A | 11/1990 | Mazur et al. |
| 5,869,783 | A | 2/1999 | Pan |
| 5,883,762 | A | 3/1999 | Calhoun et al. |
| 7,704,369 | B2 | 4/2010 | Olah et al. |
| 8,138,380 | B2 | 3/2012 | Olah et al. |
| 8,313,634 | B2 | 11/2012 | Bocarsly et al. |
| 8,357,270 | B2 | 1/2013 | Gilliam et al. |
| 8,414,758 | B2 | 4/2013 | Deguchi et al. |
| 8,449,652 | B2 | 5/2013 | Radosz et al. |
| 8,500,987 | B2 | 8/2013 | Teamey et al. |
| 8,524,066 | B2 | 9/2013 | Sivasankar et al. |
| 8,552,130 | B2 | 10/2013 | Lewandowski et al. |
| 8,562,811 | B2 | 10/2013 | Sivasankar et al. |
| 8,568,581 | B2 | 10/2013 | Sivasankar et al. |
| 8,592,633 | B2 | 11/2013 | Cole et al. |
| 8,658,016 | B2 | 2/2014 | Lakkaraju et al. |
| 8,663,447 | B2 | 3/2014 | Bocarsly et al. |
| 8,696,883 | B2 | 4/2014 | Yotsuhashi et al. |
| 8,721,866 | B2 | 5/2014 | Sivasankar et al. |
| 9,012,345 | B2 | 4/2015 | Masel et al. |
| 9,255,335 | B2 | 2/2016 | Kanan et al. |
| 9,370,773 | B2 | 6/2016 | Masel et al. |
| 9,481,939 | B2 | 11/2016 | Masel et al. |
| 9,580,824 | B2 | 2/2017 | Masel et al. |
| 2009/0014336 | A1* | 1/2009 | Olah ................ C07C 29/1518 205/450 |
| 2009/0266230 | A1 | 10/2009 | Radosz et al. |
| 2011/0114502 | A1 | 5/2011 | Cole et al. |
| 2011/0237830 | A1* | 9/2011 | Masel ................ B01J 31/0278 562/550 |
| 2012/0171583 | A1* | 7/2012 | Bocarsly ............ H01M 4/8657 429/413 |
| 2012/0186446 | A1 | 7/2012 | Bara et al. |
| 2012/0228148 | A1* | 9/2012 | Wolfowitz .............. C25B 3/04 205/462 |
| 2012/0247969 | A1 | 10/2012 | Bocarsly et al. |
| 2013/0105304 | A1* | 5/2013 | Kaczur .................. C25B 9/10 204/237 |
| 2013/0146448 | A1 | 6/2013 | Wang et al. |
| 2013/0175181 | A1 | 7/2013 | Kaczur |
| 2013/0180865 | A1 | 7/2013 | Cole et al. |
| 2013/0199937 | A1 | 8/2013 | Cole et al. |
| 2015/0171453 | A1 | 6/2015 | Chikashige et al. |
| 2015/0174570 | A1* | 6/2015 | Loveless .............. B01J 38/12 585/408 |
| 2015/0345034 | A1 | 12/2015 | Sundara et al. |
| 2016/0107154 | A1* | 4/2016 | Masel .................. B01J 41/14 252/62.2 |
| 2016/0108530 | A1 | 4/2016 | Masel et al. |

FOREIGN PATENT DOCUMENTS

| | | |
|---|---|---|
| WO | 2010063624 A1 | 6/2010 |
| WO | WO2016039999 A1 | 3/2016 |
| WO | WO2016064440 A1 | 4/2016 |
| WO | WO2016064447 A1 | 4/2016 |

OTHER PUBLICATIONS

Lin et al., "Alkaline Stable C2-Substituted Imidazolium-Based Anion-Exchange Membranes", Chem. Mater. 25 (2013), pp. 1858-1867.*

Zhang et al., "Imidazolium functionalized polysulfone anion exchange membrane for fuel cell application", J. Mater. Chem. 21 (2011), pp. 12744-12752.*

Dewulf et al., "The electrochemical reduction of CO2 to CH4 and C2H4 at cu/nafion electrodes (solid polymer electrolyte structures)", Catalysis Letters 1 (1988), pp. 73-80.

Kaneco et al., "Electrochemical conversion of carbon dioxide to methane in aqueous NaHCO3 solution at less than 273 K" Electrochimica Acta 48 (2002), pp. 51-55.

Lee et al., "Humidity-sensitive properties of new polyelectrolytes based on the copolymers containing phosphonium salt and phosphine function", J. Applied Polymer Science, vol. 89, No. 4, Jul. 25, 2003, pp. 1062-1070.

Tang et al., "Poly(ionic liquid)s as New Materials for CO2 Absorption", Journal of Polymer Science Part A: Polymer, Chemistry 43 (2005), pp. 5477-5489.

Siroma et al., "Compact dynamic hydrogen electrode unit as a reference electrode for PEMFCs", J. of Power Sources 156 (2006), pp. 284-287.

Chen et al., "A Concept of Supported Amino Acid Ionic Liquids and Their Application in Metal Scavenging and Heterogeneous Catalysis", J. Am. Chem. Soc. 129 (2007), pp. 13879-13886.

Delacourt et al., "Design of an Electrochemical Cell Making Syngas (CO+H2) from CO2 and H2O Reduction at Room Temperature", J. of the Electrochemical Society 155 (2008), pp. B42-B49.

Wang et al., "Water-Retention Effect of Composite Membranes with Different Types of Nanometer Silicon Dioxide" Electrochemical and Solid-State Letters vol. 1, No. 11, Jan. 1, 2008, p. B201-B204.

(56) References Cited

OTHER PUBLICATIONS

Luo et al., "Quaternized poly(methyl methacrylate-co-butyl acrylate-co-vinylbenzyl chloride) membrane for alkaline fuel cells", J. Power Sources. 195 (2010), pp. 3765-3771.
Tsutsumi et al., "A Test Method of a PEFC Single Cell with Reference Electrodes", Electrical Engineering in Japan, vol. 172, No. 1 (2010), pp. 1020-1026.
Narayanan et al., "Electrochemical Conversion of Carbon Dioxide to Formate in Alkaline Polymer Electrolyte Membrane Cells", J. of the Electrochemical Society, vol. 158, No. 2, Nov. 17, 2010, pp. A167-A173.
Li et al., "Novel anion exchange membranes based on polymerizable imidazolium salt for alkaline fuel cell applications", J. Mater. Chem., vol. 21, No. 30, Jan. 1, 2011, pp. 11340-11346.
Rosen et al., "Ionic Liquid—Mediated Selective Conversion of $CO_2$ to CO at Low Overpotentials", Science 334 (2011) pp. 643-644.
Weber et al., "Thermal and Ion Transport Properties of Hydrophilic and Hydrophobic Polymerized Styrenic Imidazolium Ionic Liquids", J. of Polymer Sci.: Part B: Polymer Phy. 49 (2011) pp. 1287-1296.
Sarode et al., "Designing Alkaline Exchange Membranes from Scratch", The Electrochemical Society, 220th ECS Meeting (2011).
Zhang et al., "Imidazolium functionalized polysulfone anion exchange membrane for fuel cell application", J. Mater. Chem. 21, Sep. 14, 2011, pp. 12744-12752.
Aeshala et al., "Effect of solid polymer electrolyte on electrochemical reduction of $CO_2$", Separation and Purification Technology 94 (2012), pp. 131-137.
Deavin et al., "Anion-Exchange Membranes for Alkaline Polymer Electrolyte Fuel Cells: Comparison of Pendent Benzyltrimethylammonium- and Benzylmethylimidazolium-Head-Groups", Energy Environ. Sci. 5 (2012), pp. 8584-8597.
Oh, "Synthesis and Applications of Imidazolium-Based Ionic Liquids and Their Polymer Derivatives", Dissertation at the Missouri University of Science and Technology (2012).
Qiu et al., "Alkaline Imidazolium- and Quaternary Ammonium-Functionalized Anion Exchange Membranes for Alkaline Fuel Cell Applications", J. Mater. Chem. 22 (2012), pp. 1040-1045.
Rosen et al., "In Situ Spectroscopic Examination of a Low Overpotential Pathway for Carbon Dioxide Conversion to Carbon Monoxide", J. of Physical Chemistry 116 (2012), pp. 15307-15312.
Aeshala et al., "Effect of cationic and anionic solid polymer electrolyte on direct electrochemical reduction of gaseous $CO_2$ to fuel", Journal of $CO_2$ Utilization 3-4 (2013), pp. 49-55.
Carmo et al., "A comprehensive review on PEM water electrolysis", International J. of Hydrogen Energy 38 (2013), pp. 4901-4934.
Genovese et al., "A gas-phase electrochemical reactor for carbon dioxide reduction back to liquid fuels", AIDIC Conference Series 11 (2013), pp. 151-160.
Hickner et al., "Anion Exchange Membranes: Current Status and Moving Forward", J. of Polymer Sci. 51 (2013), pp. 1727-1735.
Prakash et al., "Electrochemical reduction of $CO_2$ over Sn-Nafion coated electrode for a fuel-cell-like device", J. of Power Sources 223 (2013), pp. 68-73.
Rosen et al., "Low temperature electrocatalytic reduction of carbon dioxide utilizing room temperature ionic liquids", Dissertation at the University of Illinois (2013).
Rosen et al., "Water Enhancement of $CO_2$ Conversion on Silver in 1-Ethyl-3-Methylimidazolium Tetrafluoroborate", J. of the Electrochemical Society 160 (2013), pp. H138-H141.
Shironita et al., "Feasibility investigation of methanol generation by $CO_2$ reduction using Pt/c-based membrane electrode assembly for a reversible fuel cell", J. of Power Sources 228 (2013), pp. 68-74.
Shironita et al., "Methanol generation by $CO_2$ reduction at a PteRu/C electrocatalyst using a membrane electrode assembly", J. of Power Sources 240 (2013), pp. 404-410.
Thorson et al., "Effect of Cations on the Electrochemical Conversion of $CO_2$ to CO", J. of the Electrochemical Society 160 (2013), pp. F69-F74.
Wu et al., "Electrochemical Reduction of Carbon Dioxide", J. of the Electrochemical Society 160 (2013), pp. F953-F957.
Chen et al., "Composite Blend Polymer Membranes with Increased Proton Selectivity and Lifetime for Vanadium Redox Flow Batteries", J. of Power Sources, vol. 231, Jan. 9, 2013, pp. 301-306.
Lin et al., "Alkaline Stable C2-Substituted Imidazolium-Based Anion-Exchange Membranes", Chem. Mater. vol. 25, No. 9, May 14, 2013, pp. 1858-1867.
Yan et al. "Imidazolium-functionalized poly(ether ether ketone) as membrane and electrode ionomer for low-temperature alkaline membrane direct methanol fuel cell", Journal of Power Sources, vol. 250, Nov. 8, 2013, pp. 90-97.
Aeshala et al., "Electrochemical conversion of $CO_2$ to fuels: tuning of the reaction zone using suitable functional groups in a solid polymer electrolyte", Phys. Chem. Chem. Phys. 16 (2014), pp. 17588-17594.
Carlisle et al., "Vinyl-Functionalized Poly(imidazolium)s: A Curable Polymer Platform for Cross-Linked Ionic Liquid Gel Synthesis", Chem. Mater. 26 (2014), pp. 1294-1296.
Ma et al., "Efficient Electrochemical Flow System with Improved Anode for the Conversion of $CO_2$ to CO", J. of the Electrochemical Society 161 (2014), pp. F1124-F1131.
Parrondo et al., "Degradation of Anion Exchange Membranes Used for Hydrogen Production by Ultrapure Water Electrolysis", Royal Soc. of Chem. Adv. 4 (2014), pp. 9875-9879.
Said et al., "Functionalized Polysulfones as an Alternative Material to Improve Proton Conductivity at Low Relative Humidity Fuel Cell Applications", Chemistry and Materials Research 6 (2014), pp. 19-29.
Shi et al., "A novel electrolysis cell for $CO_2$ reduction to CO in ionic liquid/organic solvent electrolyte", Journal of Power Sources 259 (2014) pp. 50-53.
Varcoe et al., "Anion-exchange membranes in electrochemical energy systems", Energy Environ. Sci. 7 (2014), pp. 3135-3191.
Kim et al., "Influence of dilute feed and pH on electrochemical reduction of $CO_2$ to Co on Ag in a continuous flow electrolyzer", Electrochimica Acta 166 (2015), pp. 271-276.
Schauer et al., "Polysulfone-based anion exchange polymers for catalyst binders in alkaline electrolyzers", Journal of Applied Polymer Science (2015), pp. 1-7.
International Search Report and Written Opinion dated Jul. 6, 2015, in connection with International Application PCT/US2015/014328.
International Search Report and Written Opinion dated Jul. 20, 2015, in connection with International Application PCT/US2015/026507.
Restriction Requirement dated Jul. 30, 2015, in connection with related U.S. Appl. No. 14/704,935 (Having an PTO-892).
Non-Final Office Action issued by the USPTO dated Oct. 26, 2015, in connection with related U.S. Appl. No. 14/704,935.
Non-Final Office Action issued by the USPTO dated Dec. 1, 2015, in connection with related U.S. Appl. No. 14/704,934.
Final Office Action issued by the USPTO dated Apr. 27, 2016, in connection with related U.S. Appl. No. 14/704,934.
Office Action issued by the Korean IP Office on Sep. 13, 2016, in connection with Korean Patent Application No. 10-2016-7022952.
Partial International Search Report dated Nov. 24, 2016, in connection with International Application PCT/US2016/045210.
International Search Report and Written Opinion dated Jan. 20, 2017, in connection with International Application No. PCT/US2016/045210.
Non-Final Office Action dated Mar. 22, 2017, in connection with U.S. Appl. No. 15/158,227.
International Preliminary Report on Patentability dated May 4, 2017, in connection with International Application No. PCT/US2015/014328.
International Preliminary Report on Patentability dated May 4, 2017, in connection with International Application No. PCT/US2015/026507.
Non-Final Office Action dated May 26, 2017, in connection with U.S. Appl. No. 15/400,775.
Office Action issued by the Korean IP Office on May 29, 2017, in connection with Korean Patent Application No. 10-2016-7022952.

(56) References Cited

OTHER PUBLICATIONS

Partial International Search Report dated Jun. 22, 2017, in connection with International Application PCT/US2017/025624.
Patent Examination Report dated Jun. 29, 2017, in connection with Australian Application No. 2015337093.
International Search Report and Written Opinion dated Jul. 12, 2017, in connection with International Application PCT/US2017/025628.
International Search Report and Written Opinion dated Jul. 28, 2017, in connection with related International Application No. PCT/US2014/025626.
International Search Report and Written Opinion dated Aug. 16, 2017, in connection with International Application PCT/US2017/025624.
Notice of Allowance dated Aug. 22, 2017, in connection with U.S. Appl. No. 15/400,775.
Non-Final Office Action dated Sep. 1, 2017, in connection with U.S. Appl. No. 15/260,213.
Office Action issued by the Canadian IP Office dated Sep. 13, 2017, in connection with International Application.
Non-Final Office Action dated Sep. 22, 2017, in connection with U.S. Appl. No. 15/158,227.
Zhu et al., "Supported Choline Chloride/Urea as a Heterogeneous Catalyst for Chemical Fixation of Carbon Dioxide to cyclic Carbonates", Green Chem. 9 (2007), pp. 169-172.
Examination Report dated Feb. 27, 2018 in connection with Indian Application No. 733/CHENP/2013.
Office Action dated Mar. 13, 2018 in connection with European Application No. 15722607.7.
Raebiger et al., "Electrochemical Reduction of CO2 to CO Catalyzed by a Bimetallic Palladium Complex", Organometallics 25 (2006), pp. 3345-3351.
Japanese Office Action dated Jan. 30, 2018 in connection with Japanese Application No. 2016-238639.
Office Action dated May 23, 2018 in connection with Canadian Application No. 2,941,423.
Office Action dated Jun. 26, 2018 in connection with Australian Application No. 2015337093.

* cited by examiner

SYSTEM AND PROCESS FOR THE PRODUCTION OF RENEWABLE FUELS AND CHEMICALS

CROSS-REFERENCE TO RELATED APPLICATIONS

The present application is related to and claims priority benefits from U.S. provisional patent application Ser. No. 62/380,917 filed on Aug. 29, 2016, entitled "Renewal Fuel Production Systems and Process".

The present application is also continuation-in-part of U.S. patent application Ser. No. 15/158,227 filed on May 18, 2016, entitled "Catalyst Layers and Electrolyzers". The '227 application is, in turn, a continuation-in-part of U.S. patent application Ser. No. 14/704,935 filed on May 5, 2015, now U.S. Pat. No. 9,370,773 issued on Jun. 21, 2016, entitled "Ion-Conducting Membranes".

The present application is continuation-in-part of U.S. patent application Ser. No. 15/400,775 filed on Jan. 6, 2017, entitled "Ion-Conducting Membranes". The '775 patent is a continuation-in-part of U.S. patent application Ser. No. 15/090,477, filed on Apr. 4, 2016, now U.S. Pat. No. 9,580,824 issued on Feb. 28, 2017, also entitled "Ion-Conducting Membranes".

This application is also related to U.S. patent application Ser. No. 14/035,935, filed on Sep. 24, 2013, entitled "Devices and Processes for Carbon Dioxide Conversion into Useful Fuels and Chemicals" (now U.S. Pat. No. 9,370,733); U.S. patent application Ser. No. 12/830,338, filed on Jul. 4, 2010, entitled "Novel Catalyst Mixtures"; International application No. PCT/2011/030098 filed Mar. 25, 2011, entitled "Novel Catalyst Mixtures"; U.S. patent application Ser. No. 13/174,365, filed Jun. 30, 2011, entitled "Novel Catalyst Mixtures"; International application No. PCT/US2011/042809, filed Jul. 1, 2011, entitled "Novel Catalyst Mixtures"; U.S. patent application Ser. No. 13/530,058, filed Jun. 21, 2012, entitled "Sensors for Carbon Dioxide and Other End Uses"; International application No. PCT/US2012/043651, filed Jun. 22, 2012, entitled "Low Cost Carbon Dioxide Sensors"; and U.S. patent application Ser. No. 13/445,887, filed Apr. 12, 2012, entitled "Electrocatalysts for Carbon Dioxide Conversion".

STATEMENT OF GOVERNMENT INTEREST

This invention was made, at least in part, with U.S. government support under Department of Energy Contract No. DE-SC0015940. The government has certain rights in the invention.

FIELD OF THE INVENTION

The present invention relates to a system that can easily be switched from the production of renewable fuels to the production of renewable chemicals, and that uses a $CO_2$ electrolyzer with a special membrane that enables $CO_2$ electrolysis to be accomplished at temperatures up to 120° C.

Generally, the process will involve the use of carbon dioxide and water electrolyzers to produce a mixture of carbon monoxide and hydrogen that promotes the production of fuels or that promotes the production of chemicals. The process will then use a series of reactors to produce a desired product.

BACKGROUND OF THE INVENTION

Economic methods for producing modest quantities of renewable chemicals have been sought for years. The production of renewable chemicals would enable the U.S. to become more sustainable, but the present production costs are too high. The question is largely one of scale. The costs could be lowered if the products were made at a large scale. But the present markets are too small to justify the investment in a large-scale plant.

The situation is different for renewable fuels. The United States has made the deployment of systems and facilities to generate renewable fuels and chemicals a major priority. The Energy Independence and Security Act of 2007 (EISA) calls for the U.S. to produce 24 billion gallons (ethanol equivalent) of renewable fuel by 2017. The U.S. Environmental Protection Agency (EPA) has proposed lowering that amount to 18.8 billion gallons, because technological advances are required to produce the additional 5.2 billion gallons of renewable fuel. The situation could be even worse in 2022, when the EISA has set 36 billion gallons of renewable fuel as the production target. Stepping up the production of cellulosic ethanol cannot fill this gap because the "blend wall" (the maximum ethanol concentration allowed in fuel for gasoline-burning combustion engines) has already been reached. In this regard, ethanol is at the blend maximum of 10 parts ethanol to 90 parts gasoline to remain suitable for use in combustion engines, and there are no practical alternatives to ethanol at present. No other existing commercial scale technology can fill the gap. New technological solutions are therefore needed.

The economics associated with the production of renewable fuel are also favorable. The EISA set up a trading system for Renewable Identification Number (RIN) certificates, where one RIN is awarded for each gallon of "ethanol equivalent" fuel produced. If one produces renewable gasoline, then each gallon of gasoline would be awarded 1.56 RINs. "D3" RINs currently sell for about $2.70/gallon. California has a related low carbon fuel certificate (LCFS), by which the producer is awarded one LCFS certificate for each metric ton (MT) of $CO_2$ that is converted into fuel. A California LCFS certificate currently sell for $70. Calculations indicate that the sales of certificates from a 150 megawatt (MW) electrolyzer-based renewable gasoline plant would generate over $42,000,000 of revenue ($1.63/gal), thereby lowering the net cost of producing gasoline using the present system.

The net effect is the cost to produce renewable fuels approaching economic viability.

Missing at present is a way to take advantage of the growing market for renewable fuels to also produce renewable chemicals. For example, it is possible to imagine constructing a large plant that can produce either renewable fuels or renewable chemicals. In that way, the plant could serve two markets, so the cost of the plant construction could be divided over the two markets. Such a large-scale plant does not exist today, but if it could be built, it would serve the renewable fuel market and would also lower the cost of the renewable chemicals, to help that market develop.

SUMMARY OF THE INVENTION

Shortcomings of existing systems and processes for producing quantities of renewable fuels and chemicals are overcome by a production system and process that allows convenient switching between making renewable chemicals and making renewable fuels. The system comprises:
 (a) a $CO_2$ electrolyzer for converting $CO_2$ to CO;
 (b) a water electrolyzer for converting $H_2O$ to $H_2$;
 (c) a mix point to combine the output of the $CO_2$ and water electrolyzers;

(d) a control unit to vary the ratio of $CO_2$ to $H_2$ according to which product is being produced; and (e) a series of reactors for converting CO produced by the $CO_2$ electrolyzer and $H_2$ produced by the water electrolyzer to fuels, chemicals, or fuels and chemicals.

Preferably the $CO_2$ electrolyzer comprises an anion-conducting polymeric membrane.

In one embodiment, the anion conducting membrane comprises a terpolymer of styrene, vinylbenzyl-Rs and vinylbenzyl-Rx, where:
(a) Rs is a positively charged cyclic amine group,
(b) Rx is at least one constituent selected from the group consisting of Cl, OH and a reaction product between an OH or Cl and a species other than a simple amine or a cyclic amine, and
(c) the total weight of the vinylbenzyl-Rx groups is greater than 0.3% of the total weight of the membrane.

In an alternate preferred embodiment, the anion conducting membrane comprises a polymer blend or mixture of a copolymer consisting essentially of styrene and vinylbenzyl-Rs with at least one polymeric constituent selected from the group consisting of:
(a) a linear or substituted non-aromatic polyolefin;
(b) a polymer comprising cyclic amine groups;
(c) a polymer, excluding polystyrene, comprising at least one of a phenylene group and a phenyl group;
(d) a polyamide; and
(e) the reaction product of styrene and vinylbenzyl-Rs monomers with a crosslinking monomer having two carbon-carbon double bonds.

Rs is a preferably positively charged cyclic amine group, and the total weight of the at least one polymeric constituent in the membrane is less than the weight of the copolymer in the membrane.

Rs is preferably tetra-methyl-imidazolium.

The fuel produced by the foregoing system can be synthetic gasoline, diesel, jet fuel and/or avgas.

The chemicals produced by the foregoing system are preferably alcohols, olefins, or ethers, most preferably ethylene, propylene, or mixtures thereof.

Preferably, the $CO_2$ electrolyzer runs at temperatures above 25° C., preferably above 35° C., most preferably above 40° C.

Preferably, a suitable membrane for the $CO_2$ electrolyzer satisfies the following test:
(1) A cathode is prepared as follows:
(a) Silver ink is made as follows. A mixture of 2 mg carbon black (for example, Vulcan XC 72RXC72, from Fuel Cell Earth), 0.2 ml of a 1% solution of the membrane polymer and 0.5 ml ethanol (SigmaAldrich, USA) is sonicated for 5 minutes. 100 mg of silver nanoparticles (for example, 20-40 nm, 45509, Alfa Aesar, Ward Hill, Mass.) with 1.5 ml ethanol are added and then sonicated for 5 more minutes.
(b) The silver ink is then hand-painted onto a gas diffusion layer (for example, Sigracet 35 BC GDL, Ion Power Inc., New Castle, Del.) covering an area of 5 cm×5 cm. It is sintered at 80° C. for 15 minutes, followed by 120° C. for 15 minutes. It is then soaked in a 1 M KOH bath for 1 hour with the painted side face down.
(2) An anode is prepared as follows:
(a) $IrO_2$ ink is made by mixing 100 mg of $IrO_2$ (Alfa Aesar) with 1 ml deionized water (18.2 Mohm Millipore), 2 ml isopropanol (3032-16, Macron) and 0.101 ml of 5% Nafion solution (1100EW, DuPont, Wilmington, Del.).
(b) The $IrO_2$ ink is then hand-painted onto a 5% wet proofed carbon fiber paper (for example, TGP-H-120 5% Teflon Treated Toray Paper, from Fuel Cell Earth) covering an area of 6 cm×6 cm. Then, the carbon paper is sintered at 80° C. for 30 min.
(3) A 50-300 micrometer thick membrane of a "test" material is made by conventional means such as casting or extrusion.
(4) The membrane is sandwiched between a 3×3 cm piece of the anode material and a 2.5×2.5 cm piece of the cathode material with the metal layers on the anode and cathode facing the membrane.
(5) The membrane electrode assembly is mounted in Fuel Cell Technologies (Albuquerque, N. Mex.) 5 cm² fuel cell hardware assembly with serpentine flow fields.
(6) $CO_2$ humidified at 65° C. is fed into the cathode at a rate of 20 sccm and 10 mM $KHCO_3$ is fed into the anode flow field at a flow rate of 3 ml/min.
(7) The cell is heated to 50° C., and a power supply is connected.
(8) The cell is maintained at 3 V for 2 hours, then is switched to constant current mode at 200 mA/cm².
(9) The cell is maintained in constant current mode for at least 100 hours.
(10) Selectivity is calculated as follows:

$$\text{Selectivity} = \frac{(\text{CO production rate})}{(\text{CO production rate} + H_2 \text{ production rate})}$$

where the CO and $H_2$ production rates are measured in standard cubic centimeters per minute (sccm) leaving the electrolyzer. If Selectivity is greater than 90%, and the voltage to maintain 200 mA/cm² is less than 3 V, the membrane is suitable.

The series of reactors preferably includes at least 3 reactors.

The series of reactors preferably includes a first reactor that converts the CO and $H_2$ to methanol, then the methanol is converted dimethyl ether in a second reactor, and the dimethyl ether is converted in a third reactor to a synthetic fuel and/or a chemical.

The conversion of dimethyl ether to a synthetic fuel and/or a chemical preferably employs a zeolite catalyst such as ZSM-5 or SAPO-34.

The zeolite preferably consists of material with an $SiO_2$/$Al_2O_3$ weight ratio of 2 to 9, a Brunauer-Emmett-Teller (BET) surface of 250 to 500 m²/g, and an Na content under 200 ppm, such as the catalyst described in U.S. Pat. No. 9,174,204.

A process for the production of renewable fuel in a $CO_2$ collection unit for extracting $CO_2$ from a sustainable source:
(a) converting $CO_2$ to CO via a $CO_2$ electrolyzer;
(b) converting $H_2O$ to $H_2$ via a water electrolyzer; and
(c) converting CO produced via the $CO_2$ electrolyzer and $H_2$ produced via the water electrolyzer to a fuel.

The fuel produced by the foregoing process can be synthetic gasoline and/or diesel, jet fuel and/or avgas (aviation gasoline).

The sustainable source of $CO_2$ can be atmospheric air or $CO_2$ output from a fermenter, a municipal waste treatment facility, a wood processing unit, or a landfill.

The extracted $CO_2$ in the foregoing process is preferably substantially pure. The $H_2$ produced in the foregoing process is also preferably substantially pure. More preferably, both the extracted $CO_2$ and the $H_2$ produced in the foregoing process are substantially pure.

DETAILED DESCRIPTION OF ILLUSTRATIVE EMBODIMENT(S)

Figure 1:
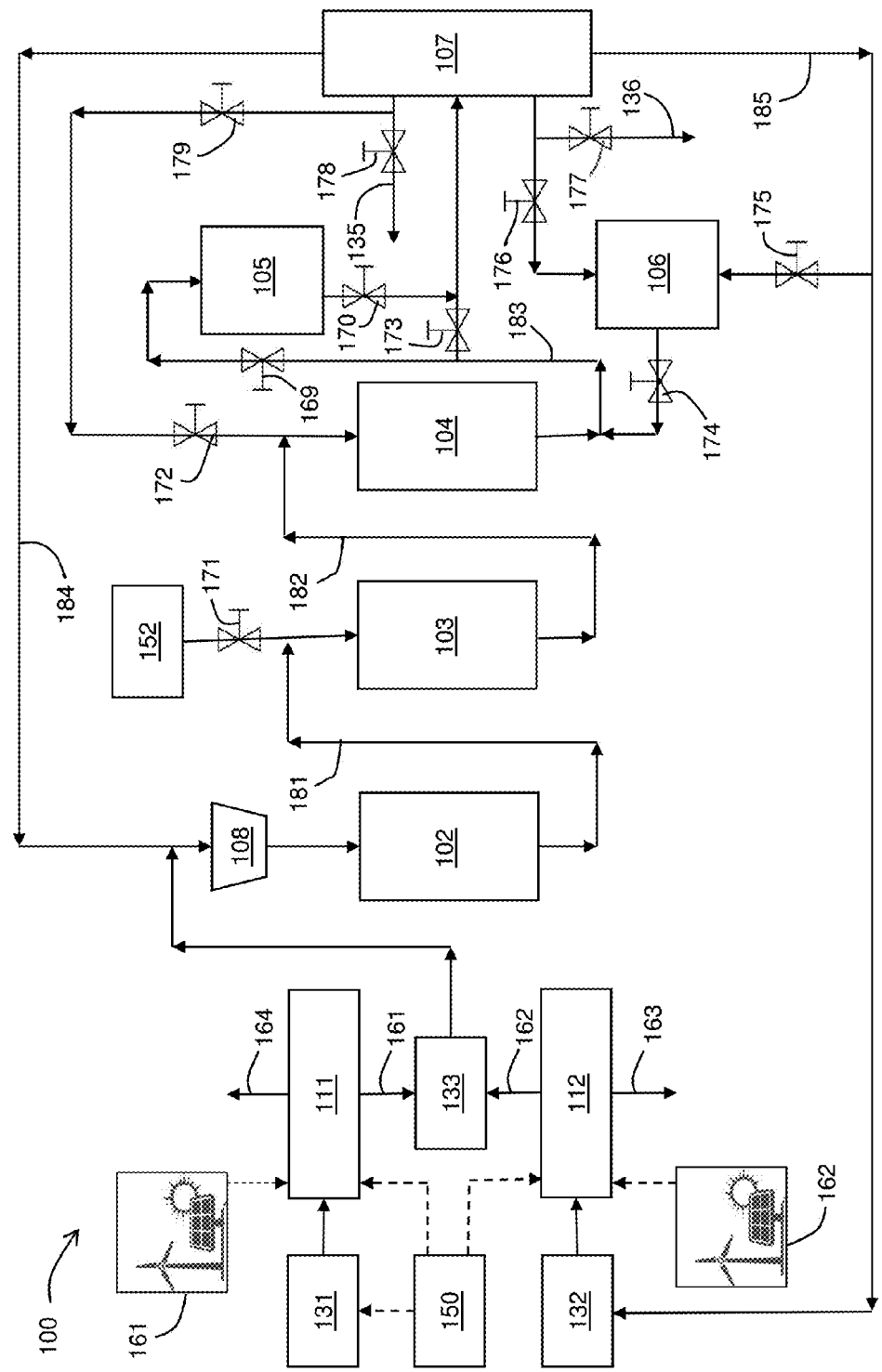
FIG. 1 is a schematic diagram of the present renewable fuel production system.

The present production system converts air, water, and renewable electricity into renewable fuel and/or chemicals. The system includes the following subsystems:
- a $CO_2$ electrolyzer for converting $CO_2$ to CO (and $O_2$);
- a water electrolyzer for converting $H_2O$ to $H_2$ (and $O_2$);
- a controller to adjust the ratio of CO and $H_2$ produced by the electrolyzers; and
- a series of reactors for converting CO produced by the $CO_2$ electrolyzer and $H_2$ produced by the water electrolyzer to fuels and/or chemicals.

These subsystems have demonstrated reactant production and economic efficiencies that make their combination advantageous for the production of gasoline.

Provided immediately below is a Definitions section, where certain terms related to the process are defined specifically. Particular methods, devices, and materials are described, although any methods and materials similar or equivalent to those described herein can be used in the practice or testing of the process.

Definitions

The term "electrochemical conversion of $CO_2$" as used herein refers to any electrochemical process in which carbon dioxide, carbonate, or bicarbonate is converted into another chemical substance in any step of the process.

The term "polymer electrolyte membrane" as used herein refers to both cation exchange membranes, which generally comprise polymers having multiple covalently attached negatively charged groups, and anion exchange membranes, which generally comprise polymers having multiple covalently attached positively charged groups. Typical cation exchange membranes include proton conducting membranes, such as the perfluorosulfonic acid polymer available under the trade designation NAFION from E. I. du Pont de Nemours and Company (DuPont) of Wilmington, Del.

The term "anion exchange membrane electrolyzer" as used herein refers to an electrolyzer with an anion-conducting polymer electrolyte membrane separating the anode from the cathode.

The term "liquid free cathode" refers to an electrolyzer where there are no bulk liquids in direct contact with the cathode during electrolysis. There can be a thin liquid film on or in the cathode, however, and occasional washes or rehydration of the cathode with liquids could occur.

The term "faradaic efficiency" as used herein refers to the fraction of the electrons applied to the cell that participate in reactions producing carbon-containing products.

The term "MEA" as used herein refers to a membrane electrode assembly.

The term "GC" as used herein refers to a gas chromatograph.

The term "imidazolium" as used herein refers to a positively charged ligand containing an imidazole group. This includes a bare imidazole or a substituted imidazole. Ligands of the form:

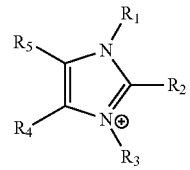

where $R_1$-$R_5$ are each independently selected from hydrogen, halides, linear alkyls, branched alkyls, cyclic alkyls, heteroalkyls, aryls, heteroaryls, alkylaryls, heteroalkylaryls, and polymers thereof, such as the vinyl benzyl copolymers described herein, are specifically included.

The term "pyridinium" as used herein refers to a positively charged ligand containing a pyridine group. This includes a bare pyridine or a substituted pyridine. Ligands of the form:

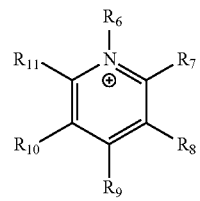

where $R_6$-$R_{11}$ are each independently selected from hydrogen, halides, linear alkyls, branched alkyls, cyclic alkyls, heteroalkyls, aryls, heteroaryls, alkylaryls, heteroalkylaryls, and polymers thereof, such as the vinyl benzyl copolymers described herein, are specifically included.

The term "phosphonium" as used herein refers to a positively charged ligand containing phosphorous. This includes substituted phosphorous. Ligands of the form:

$P^+(R_{12}R_{13}R_{14}R_{15})$ where $R_{12}$-$R_{15}$ are each independently selected from hydrogen, halides, linear alkyls, branched alkyls, cyclic alkyls, heteroalkyls, aryls, heteroaryls, alkylaryls, heteroalkylaryls, and polymers thereof, such as the vinyl benzyl copolymers described herein, are specifically included.

The term "positively charged cyclic amine" as used herein refers to a positively charged ligand containing a cyclic amine. This specifically includes imidazoliums, pyridiniums, pyrazoliums, pyrrolidiniums, pyrroliums, pyrimidiniums, piperidiniums, indoliums, triaziniums, and polymers thereof, such as the vinyl benzyl copolymers described herein.

The term "PSTMIM Solution" as referred herein refers to a solution prepared as described in Specific Example 3 herein.

The term "sustainable source" as used herein refers to a source of $CO_2$ other than a $CO_2$ well or other natural $CO_2$ source. Sustainable sources specifically include $CO_2$ captured from the air, $CO_2$ from a fermenter, $CO_2$ from a municipal waste facility and $CO_2$ from a landfill.

The term "and/or" as used herein means "either or both".

Specific Example 1: Basic System Design

FIG. 1 is a schematic flow diagram of the present renewable fuel production system 100. System 100 includes electrolyzers 111 and 112, reactors 102, 103, 104, 105 and 106, separator 107, compressor 108, valves 169, 170, 171, 172, 173, 174, 175, 176, 177, 178 and 179, controller 150, and mix point 133. As further shown in FIG. 1, system 100 also includes a source of renewable $CO_2$ 131, a source of water 132, a source of bio-methanol 152, a combined CO and $CO_2$ stream 161 exiting electrolyzer 111 and directed to mix point 133, an $H_2$ stream 162 exiting electrolyzer 112 and directed to mix point 133, an $O_2$ outlet stream 163 exiting electrolyzer 112, and an $O_2$ outlet stream 164 exiting electrolyzer 111. A methanol stream 181 exits reactor 102 and is directed to the inlet stream of reactor 103. A dimethyl ether stream 182 exits reactor 103 and is directed to the inlet stream of reactor 104. A combined gasoline, propylene and tar stream 183 exits reactor 104 and is directed to the inlet stream of reactor 105 and/or to the inlet stream of separator 107. The streams exiting separator 107 include propylene exit stream 135, gasoline exit stream 136, a combined $H_2$, CO and $CO_2$ stream 184 and an $H_2O$ stream 185. A renewable energy source 161 powers electrolyzer 111. A renewable energy source 162 powers electrolyzer 112.

Electrolyzer 111 converts $CO_2$ to CO via the reaction $CO_2 \rightarrow CO + \frac{1}{2} O_2$. A preferred design is set forth in Example 1 of co-owned U.S. Pat. No. 9,481,939.

Electrolyzer 112 converts $H_2O$ to $H_2$ via the reaction $H_2O \rightarrow H_2 + \frac{1}{2} O_2$. A preferred design is set forth in co-owned U.S. patent application Ser. No. 15/406,909.

Controller 150 adjusts the ratio of CO, $H_2$, $CO_2$ and $H_2O$.

Mix point 133 is designed to mix the output streams from the $CO_2$ and water electrolyzers.

Reactor 102 converts mixtures of CO, $CO_2$ and $H_2$ to methanol. Reactor 102 preferably contains a Cu/ZnO catalyst such as MK-151 FENCE™ from Haldor-Topsoe (Linyi, Denmark).

Reactor 103 converts methanol to dimethyl ether. Reactor 103 preferable contains a $\gamma$-$Al_2O_3$ catalyst such as BASF G-250 catalyst.

Reactor 104 converts dimethyl ether to either olefins, such as propylene, or into gasoline. Reactor 104 preferably contains a zeolite catalyst such as ZSM-5 or SAPO-34. Most preferably, the zeolite consists of material with an $SiO_2$/$Al_2O_3$ weight ratio of 2 to 9, a BET surface of 250 to 500 $m^2$/g, and an Na content under 200 ppm, such as the catalyst described in U.S. Pat. No. 9,174,204.

Reactor 105 hydrogenates durene and other tar molecules. Reactor 105 preferably contains a nickel on alumina catalyst such as Criterion KL6515, or a cobalt molybdate on alumina catalyst, such as Alfa Aesar 45579.

Reactor 106 converts the $C_5^+$ molecules (molecules containing 5 or more carbons) back to CO, $H_2$ and light olefins via reaction with steam. Reactor 106 preferably contains either a ZSM-5 catalyst or a nickel on alumina catalyst.

Figure 2:
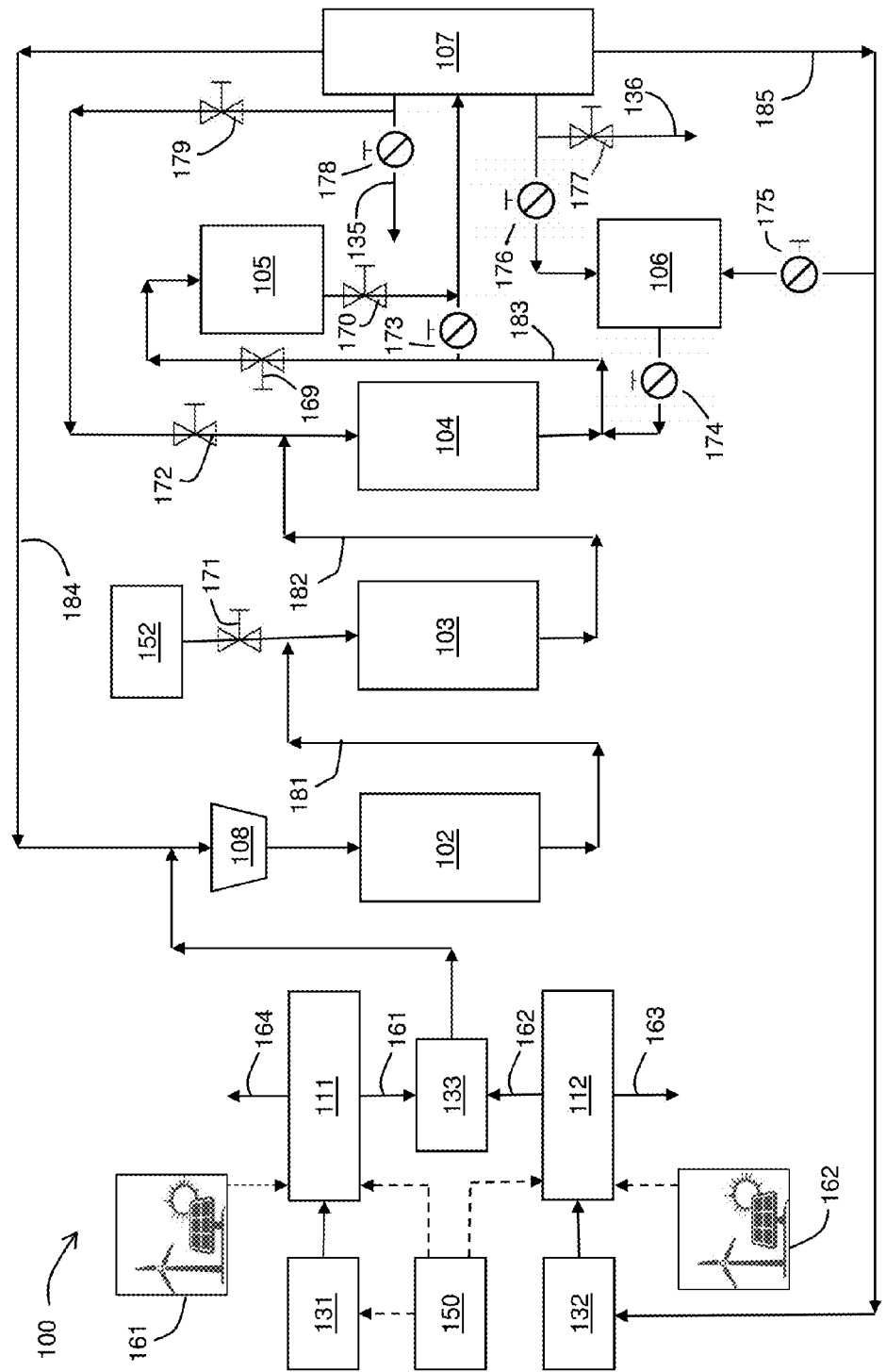
FIG. 2 is a schematic diagram of the present renewable fuel production system configured to produce mainly gasoline.

FIG. 2 illustrates operation of renewable fuel production system 100 to produce mainly fuels such as gasoline. As shown in FIG. 2, valves 173, 174, 175, 176 and 178 are closed, as depicted by the circle-and-backlash symbol (Ø) over each of those valves, and reactor 106 is shut down or placed into a regeneration cycle. In this case, the tar is hydrogenated in reactor 105 before the separation step, and olefins produced are recycled back to reactor 104 to produce more gasoline.

Figure 3:
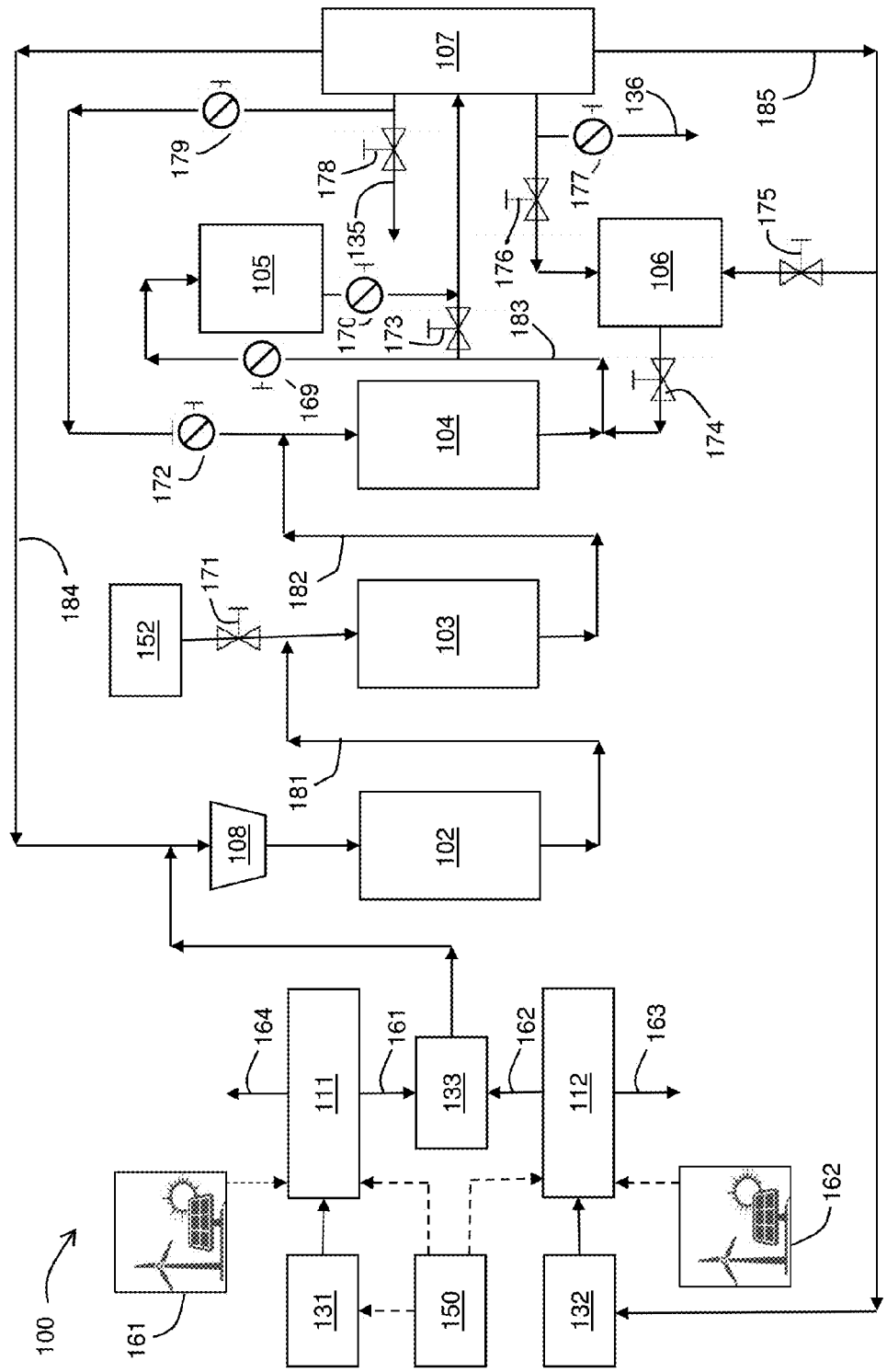
FIG. 3 is a schematic diagram the present renewable fuel production system configured to produce mainly olefins, preferable propylene.

FIG. 3 shows how the device will be operated to produce mainly olefins such as propylene. In this case valves 169, 170, 172, 177 and 179 are closed, as depicted by the circle-and-backlash symbol (Ø) over each of those valves, and reactor 105 is shut down or placed into a regeneration cycle. The controller 201 adjusts the CO, $CO_2$ to $H_2$ to promote gasoline production. In this case, the tar and gasoline is sent to reactor 106 and the gasoline, tar and other hydrocarbons are cracked to produce light olefins, CO, $CO_2$ and $H_2$.

The advantages of this design are:
 (a) Easy switching from making fuels to making chemicals. The chemicals have a limited market, but they are high value. Fuels have a much larger market, but they are lower value. By combining the two processes, we can take advantage of the economies of scale associated with manufacturing a high-volume product, and still also make a high value, low-volume product.
 (b) Use of electrolyzers, 111 and 112, and controller 201, allows one to adjust the ratio of the CO, $CO_2$, $H_2$ and $H_2O$ in the feed to reactor 102 to promote the production of products. For example, the preferred CO to $H_2$ ratio to produce gasoline is about 1:2.5, but, for example, steam methane reforming gives about 1:3.
 (c) The renewable fuel production system and process described herein is carbon negative and provides energy-efficient generation of energy-dense liquid fuels or chemicals from renewable energy, water and air.

Specific Example 2: Alternate System Embodiment

Figure 4:
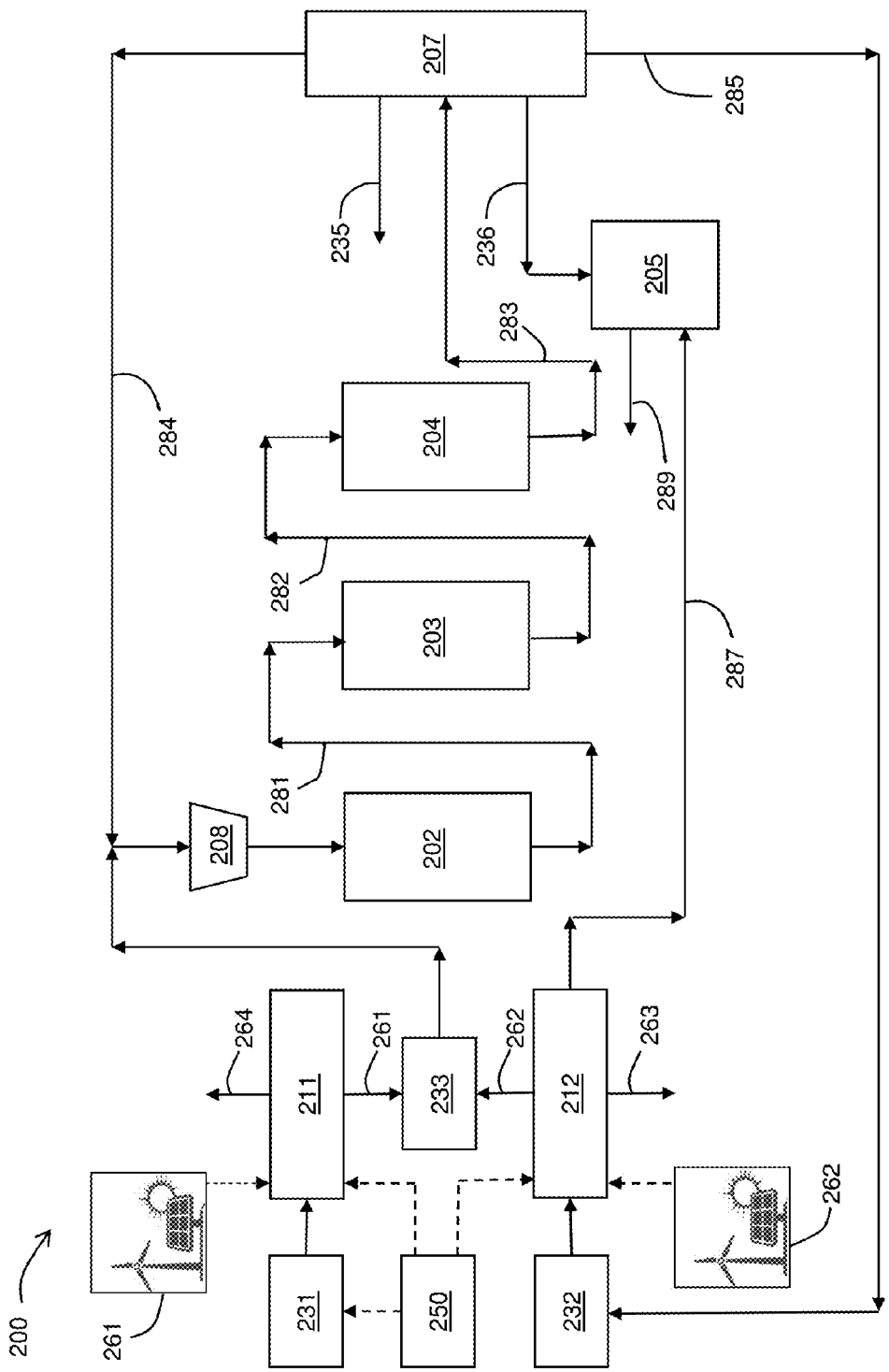
FIG. 4 is a schematic diagram of an alternate design of the present renewable fuel production system in which the system produces both gasoline and olefins.

FIG. 4 shows an alternate system embodiment 200 in which both propylene and gasoline are produced. In this embodiment, the design is simplified to omit reactor 106 in system 100 shown in FIG. 1. System 200 includes electrolyzers 211 and 212, reactors 202, 203, 204 and 205, separator 207, compressor 208, controller 250, and mix point 233. As further shown in FIG. 1, system 200 also includes a source of renewable $CO_2$ 231, a source of water 232, a combined CO and $CO_2$ stream 261 exiting electrolyzer 211 and directed to mix point 233, an $H_2$ stream 262 exiting electrolyzer 212 and directed to mix point 233, an $H_2$ stream 287 exiting electrolyzer 212 and directed to reactor 205, an $O_2$ outlet stream 263 exiting electrolyzer 212, and an $O_2$ outlet stream 264 exiting electrolyzer 211. A methanol stream 281 exits reactor 202 and is directed to the inlet stream of reactor 203. A dimethyl ether stream 282 exits reactor 203 and is directed to the inlet stream of reactor 204. A combined gasoline, propylene and tar stream 283 exits reactor 204 and is directed to the inlet stream of separator 207. The streams exiting separator 207 include propylene exit stream 235, a combined gasoline and tar exit stream 236, a combined $H_2$, CO and $CO_2$ stream 284 and an $H_2O$ stream 285. A gasoline stream 289 exists reactor 205. A renewable energy source 261 powers electrolyzer 211. A renewable energy source 262 powers electrolyzer 212.

Electrolyzer 211 converts $CO_2$ to CO via the reaction $CO_2 \rightarrow CO + \frac{1}{2} O_2$. A preferred design is set forth in Example 1 of co-owned U.S. Pat. No. 9,481,939.

Electrolyzer 212 converts $H_2O$ to $H_2$ via the reaction $H_2O \rightarrow H_2 + \frac{1}{2} O_2$. A preferred design is set forth in co-owned U.S. patent application Ser. No. 15/406,909.

Controller 250 adjusts the ratio of CO, $H_2$, $CO_2$ and $H_2O$.

Mix point 233 is designed to mix the output streams from the $CO_2$ and water electrolyzers.

Reactor 202 converts mixtures of CO, $CO_2$ and $H_2$ to methanol. Reactor 202 preferably contains a Cu/ZnO catalyst such as MK-151 FENCE™ from Haldor-Topsoe (Lyngby, Denmark).

Reactor 203 converts methanol to dimethyl ether. Reactor 203 preferable contains a $\gamma$-$Al_2O_3$ catalyst such as BASF G-250 catalyst.

Reactor 204 converts dimethyl ether to either olefins, such as propylene, or into gasoline. Reactor 104 preferably contains a zeolite catalyst such as ZSM-5 or SAPO-34. Most preferably, the zeolite consists of material with an $SiO_2$/$Al_2O_3$ weight ratio of 2 to 9, a BET surface of 250 to 500 $m^2$/g, and an Na content under 200 ppm, such as the catalyst described in U.S. Pat. No. 9,174,204.

Reactor 205 hydrogenates durene and other tar molecules. Reactor 205 preferably contains a nickel on alumina catalyst such as Criterion KL6515, or a cobalt molybdate on alumina catalyst, such as Alfa Aesar 45579.

Specific Example 3: Improved $CO_2$ Electrolyzer

The objective of this example is to demonstrate that a terpolymer of styrene, vinylbenzyl-Rs and vinylbenzyl-Rx has significant advantages as a membrane for the $CO_2$ electrolyzer, where
  (a) Rs is a positively charged cyclic amine group,
  (b) Rx is at least one constituent selected from the group consisting of Cl, OH and a reaction product between an OH or Cl and a species other than a simple amine or a cyclic amine, and
  (c) the total weight of the vinylbenzyl-Rx groups is greater than 0.3% of the total weight of the membrane.

Specific Examples 1 and 2 used the carbon dioxide electrolyzer disclosed in Example 1 in the co-owned U.S. Pat. No. 9,481,939. This electrolyzer was designed to run at 25° C. One can operate the electrolyzer at higher temperatures, but the selectivity of the conversion process to CO drops with time because the membrane in Example 1 of the '939 patent degrades. As a result, the electrolyzer in Example 1 of the '939 patent cannot give stable performance at temperatures greater than 25-30° C.

There are several advantages to operating the electrolyzers between 30° C. and 120° C., preferably between 40° C. and 90° C. The reaction rate of the $CO_2$ conversion increases as the temperature increases. It is easier to remove heat from the electrolyzer if the electrolyzer is running at temperatures above 30° C. Pure CO has an autoignition temperature of 90° C. Mixtures might not ignite until 120° C. So, from a safety standpoint, one wishes the temperature of the electrolyzer to be below 120° C., preferably below 90° C.

It is believed that there are no current examples of a $CO_2$ electrolyzer operating in the temperature range of 40° C. to 120° C. The objective of this example to provide an example electrolyzer design that allows successful operation of a polymer electrolyte membrane-based $CO_2$ electrolyzer at higher temperatures.

First, a terpolymer membrane is prepared as described in specific Example 17 in co-owned U.S. patent application Ser. No. 15/400,775 as described below.
Step 1. Production of PSTMIM Solution.

Inhibitor-free styrene was prepared by adding a volume V of styrene (Sigma-Aldrich, Saint Louis, Mo.) and a volume equal to V/4 of 4% aqueous sodium hydroxide into a separatory funnel, followed by agitating the funnel to mix the water and styrene, then decanting the styrene layer. The process was repeated five times until the water layer did not show discernible color change. The procedure was repeated using pure water instead of sodium hydroxide solution until the water layer pH was neutral. Washed styrene was put into a freezer overnight before weighing, to confirm that residual water was mainly in ice form and was then separated from styrene by filtration or decantation. 4-vinylbenzyl chloride (4-VBC) was treated in the same manner as styrene.

Poly(4-vinylbenzyl chloride-co-styrene) was then synthesized by heating a solution of inhibitor-free styrene (Sigma-Aldrich) (172.3 g, 1.65 mol) and 4-vinylbenzyl chloride (Sigma-Aldrich) (143.1 g, 0.94 mol) in chlorobenzene (Sigma-Aldrich) (250 g) at 60-65° C. in an oil bath for 22 hours under nitrogen gas with AIBN ($\alpha,\alpha'$-Azoisobutyronitrile, Sigma-Aldrich) (2.9635 g, 0.94 wt % based on the total monomers weight) as initiator. The copolymer was precipitated in methanol and washed thoroughly and dried at 60° C. overnight.

Next 1,2,4,5-tetramethylimidazole (TCI, Japan) (3.700 g, 0.0298 mol), above-synthesized poly(4-VBC-co-St) (10 g), anhydrous ethanol (17 g, Sigma-Aldrich, USA), anhydrous toluene (12.5 g, SigmaAldrich, USA), divinyl benzene (DVB, 0.2 g, 0.00154 mol in 1 g ethanol) and AIBN (0.00301 g in 0.97 g ethanol) were mixed under the protection of nitrogen flow. The mixture was stirred and heated to 78° C. for about 1 hour. When the solution turned clear, reaction temperature was decreased to 55° C. and maintained for 71 hours to obtain a membrane polymer.
Step 2. Membrane Formation The membranes were prepared by casting the polymer solutions prepared above directly onto a polyethylene terephthalate (PET) liner. The thickness of the solution on the liner was controlled by a film applicator (MTI Corporation, Richmond, Calif.) with an adjustable doctor blade. The membranes were then dried in a vacuum oven with temperature increased to 70° C. and held for 1 hour. After one more hour in the vacuum oven with temperature slowly decreased, the membrane was taken out of the oven and put into a 1 M KOH solution overnight, during which time the membrane fell from the liner. The KOH solution was changed twice, each with a few hours of immersion, to make sure the membrane chloride ions were substantially completely exchanged, so that the membranes were substantially fully converted into the hydroxide form.

A cathode material was prepared as follows. Silver ink was made as follows. A mixture of 2 mg of carbon black (Vulcan XC 72RXC72, Fuel Cell Earth), 0.2 ml of a 1% solution of the membrane polymer and 0.5 ml ethanol (SigmaAldrich, USA) was sonicated for 5 minutes. 100 mg of silver nanoparticles (20-40 nm, 45509, Alfa Aesar, Ward Hill, Mass.) with 1.5 ml ethanol were added and then sonicated for 5 more minutes. The silver ink was then hand-painted onto a gas diffusion layer (Sigracet 35 BC GDL, Ion Power Inc., New Castle, Del.) covering an area of 5 cm×5 cm. It was sintered at 80° C. for 15 min followed by 120° C. for 15 min. It was then soaked in a 1 M KOH bath for 1 hour with the painted side face down.

An anode material was prepared as follows. $IrO_2$ ink was made by mixing 100 mg of $IrO_2$ (Alfa Aesar) with 1 ml deionized water (18.2 Mohm Millipore), 2 ml isopropanol (3032-16, Macron) and 0.101 ml of 5% NAFION solution (1100EW, DuPont, Wilmington, Del.). The $IrO_2$ ink was then hand-painted onto a 5% wet proofed carbon fiber paper (TGP-H-120 5% Teflon Treated Toray Paper, Fuel Cell Earth) covering an area of 6 cm×6 cm. The ink covered carbon fiber paper was then sintered at 80° C. for 30 minutes.

The membrane was sandwiched between the a 3×3 cm piece of the anode material and a 2.5×2.5 cm piece of the cathode material with the metal layers on the anode and cathode facing the membrane, and the entire assembly was mounted in a Fuel Cell Technologies 5 cm² fuel cell hardware assembly with serpentine flow fields.

$CO_2$ humidified at 25° C. was fed into the cathode flow field at a rate of 20 sccm, and 10 mM $KHCO_3$ was fed into the anode flow field at a flow rate of 3 ml/min. Next, the cell was connected to a power supply and the cell was run at a fixed voltage of 3 V for 2 hours, then switched to constant current mode at 200 mA/cm² for 250 hours. The cell was stable for 250 hours. The selectivity was over 90%, as shown in FIG. 5 in the '775 application.

A second membrane was prepared as above and mounted in a cell as above. $CO_2$ humidified at 65° C. was fed into the cell at a rate of 30 sccm, and 10 mM $KHCO_3$ was fed into the anode flow field at a flow rate of 3 ml/min. The cell was heated to 50° C., and the power supply was connected. Again, the cell was maintained at 3 V for 2 hours, and then switched to a constant current mode at 600 mA/cm². The cell was stable for 250 hours at 600 mA/cm² with a CO selectivity over 97%.

A third membrane was prepared as above and mounted in a cell as above. $CO_2$ humidified at 65° C. was fed into the cell at a rate of 30 sccm, and 10 mM $KHCO_3$ was fed into the anode flow field at a flow rate of 3 ml/min. The cell was heated to 50° C., and the power supply was connected. Again, the cell was maintained at 3 V and the current was measured. Subsequently the temperature was raised to 60° C., 70° C., and 80° C. for 2 hours each, and the current was measured. Table 1 summarizes these results.

TABLE 1

Cell current density, measured as a function of temperature

| Temperature | Current mA/cm² |
|---|---|
| 25° C. | 200 |
| 50° C. | 570 |
| 60° C. | 700 |
| 70° C. | 800 |
| 80° C. | Initially 880 but dropped to 680 |

These results demonstrate that a $CO_2$ electrolyzer can be successfully operated at 25-80° C., preferably 50-70° C.

Specific Example 4: Supported Membrane

The objective of this example is to demonstrate that a membrane comprising a polymer blend or mixture of a copolymer consisting essentially of styrene and vinylbenzyl-$R_s$ with at least one polymeric constituent selected from the group consisting of:
(a) a linear or substituted non-aromatic polyolefin;
(b) a polymer comprising cyclic amine groups;
(c) a polymer, excluding polystyrene, comprising at least one of a phenylene group and a phenyl group;
(d) a polyamide; and
(e) the reaction product of styrene and vinylbenzyl-$R_s$ monomers with a crosslinking monomer having two carbon-carbon double bonds,
wherein $R_s$ is a positively charged cyclic amine group, and wherein the total weight of the at least one polymeric constituent in the membrane is less than the weight of the copolymer in the membrane, as described in co-owned U.S. Pat. No. 9,580,824.

Step 1. A PSTMIM solution was prepared as described in Specific Example 3.

Step 2. The PSTMIM solution was diluted to 20% solids with ethanol.

Step 3. A BKY (Geretsried, Germany) Automatic Film Applicator L was used to cast a thin film of the polymer solution onto a polypropylene backing sheet (Home Depot, Atlanta, Ga.) using a doctor blade. The solution was allowed to dry in ambient environment for 30 minutes to yield an approximately 15 micrometer thick polymer film.

Step 4. Next, a 10 µm thick porous expanded polytetrafluoroethylene (ePTFE) film (Philips Scientific Inc., Rock Hill, S.C.) was submerged for 30 minutes in a bath of ethanol to activate its surface for better wettability. The porous ePTFE film was then laid carefully taut over the deposited polymer film. The ePTFE film was also stretched in both x and y directions to fully open its pore structure as it was laid over the polymer film.)

Step 5. A 15 µm layer of the PSTMIM polymer solution was deposited on top of the ePTFE. The polymer film was left to settle for 15 minutes in ambient conditions before the whole reinforced membrane was placed in an oven at 65° C. for 60 minutes to improve adhesion of the polymer with the ePTFE. After the heating step, the membrane was then separated from the polypropylene backing sheet with the help of a razor blade and tweezers, and then activated in 1 M KOH, as described in Specific Example 3.

The resultant membrane was mounted in a cell and tested as in Specific Example 3. Table 2 shows the results of these experiments.

TABLE 2

The current density measured as a function of temperature

| Temperature | Current mA/cm² |
|---|---|
| 50° C. | 400 |
| 60° C. | 440 |
| 70° C. | 540 |
| 80° C. | 700 |
| 90° C. | 800 |

These results demonstrate that a $CO_2$ electrolyzer can be successfully operated at 25-90° C. Temperatures up to 120° C. are also viable if the electrolyzer is pressurized.

The specific order or hierarchy of steps in the methods and/or processes disclosed herein are examples of exemplary approaches. Based upon design preferences, the specific order or hierarchy of steps in the method can be rearranged while remaining within the disclosed subject matter. The accompanying method claims present elements of the various steps in a sample order, and are not necessarily meant to be limited to the specific order or hierarchy presented.

Numerical value ranges recited herein include all values from the lower value to the upper value in increments of one unit, provided that there is a separation of at least two units between a lower value and a higher value. As an example, if it is stated that the concentration of a component or value of a process variable such as, for example, size, angle, pressure, time and the like, is, for example, from 1 to 98, specifically from 20 to 80, more specifically from 30 to 70, it is intended that values such as 15 to 85, 22 to 68, 43 to 51, 30 to 32, and the like, are expressly enumerated in this specification. For values that are less than one, one unit is considered to be 0.0001, 0.001, 0.01 or 0.1 as appropriate. These are only examples of what is specifically intended and all possible combinations of numerical values between the lowest value and the highest value are to be treated in a similar manner.

While particular elements, embodiments and applications of the present invention have been shown and described, it will be understood, that the invention is not limited thereto, since modifications can be made by those skilled in the art without departing from the scope of the present disclosure, particularly in light of the foregoing teachings.

What is claimed is:

1. A system for the manufacture of renewable fuels and/or renewable chemicals comprising:
   (a) a $CO_2$ electrolyzer for converting $CO_2$ to CO and $O_2$, wherein said $CO_2$ electrolyzer has a CO selectivity of at least 90%;
   (b) a separate water electrolyzer for converting $H_2O$ to $H_2$ and $O_2$;
   (c) a control unit for directing signals to each of said electrolyzers to vary the ratio of CO to $H_2$ produced by said electrolyzers; and
   (d) a series of reactors to convert a $CO/H_2$ mixture to fuels and/or chemicals,
   wherein said $CO_2$ electrolyzer operates in the temperature range of 40° C. to 120° C.

2. A system for the manufacture of renewable fuels and/or renewable chemicals comprising:
   (a) a $CO_2$ electrolyzer for converting $CO_2$ to CO;
   (b) a water electrolyzer for converting $H_2O$ to $H_2$;
   (c) a mixer for mixing the CO with the $H_2$;
   (d) a control unit to vary the ratio of CO to $H_2$ according to which product is being produced; and
   (e) a series of reactors to convert the $CO/H_2$ mixture to fuels and/or chemicals,
   wherein said $CO_2$ electrolyzer operates in the temperature range of 40° C. to 120° C.,
   wherein said $CO_2$ electrolyzer comprises an anion-conducting polymeric membrane comprising a terpolymer of styrene, vinylbenzyl-Rs and vinylbenzyl-Rx,
   wherein Rs is a positively charged cyclic amine group,
   wherein Rx is at least one constituent selected from the group consisting of Cl, OH and a reaction product between an OH or Cl and a species other than a simple amine or a cyclic amine,
   wherein the total weight of the vinylbenzyl-Rx groups is 1-25% of the total weight of the terpolymer, and
   wherein the total weight of the vinylbenzyl-Rs groups is at least 30% of the total weight of the terpolymer.

3. The system of claim 2, wherein Rs is tetra-methyl-imidazolium.

4. The system in claim 1, wherein the system is capable of produce at least one fuel and at least one chemical.

5. The system of claim 4, wherein said fuel is at least one of synthetic gasoline, synthetic diesel, synthetic avgas, and a blend-stock therefor.

6. The system of claim 4, wherein the chemical is at least one of methanol, dimethylether, ethanol and propylene.

7. The system of claim 1, wherein said series of reactors comprises at least 3 reactors.

8. The system of claim 7, wherein a first reactor of said series of reactors converts the CO and $H_2$ to methanol, wherein a second reactor coverts methanol to dimethyl ether, and wherein a third reactor converts dimethyl ether to at least one of a synthetic fuel and a chemical.

9. The system of claim 8, wherein the reactor that converts dimethyl ether to a synthetic fuel or chemical comprises a zeolite catalyst.

10. The system of claim 9, wherein said zeolite catalyst is a micropore zeolite catalyst.

11. The system of claim 10, wherein the zeolite catalyst has an $SiO_2/Al_2O_3$ weight ratio of 2 to 9, a BET surface of 250 to 500 $m^2/g$, and an Na content under 200 ppm.

12. The system of claim 1, wherein said $CO_2$ electrolyzer comprises:
   (a) a cathode prepared as follows: Silver ink is made by mixing 2 mg carbon black, 0.2 ml of a 1% solution of the membrane polymer and 0.5 ml ethanol is sonicated for 5 minutes; 100 mg of silver nanoparticles (20-40 nm) with 1.5 ml ethanol is added and then sonicated for 5 more minutes; the silver ink is then hand-painted onto a gas diffusion layer covering an area of 5 cm×5 cm; the gas diffusion layer is sintered at 80° C. for 15 min followed by 120° C. for 15 minutes; the gas diffusion layer is then soaked in a 1 M KOH bath for 1 hour with the painted side face down; and
   (b) an anode prepared as follows: $IrO_2$ ink is made by mixing 100 mg of $IrO_2$ with 1 ml deionized water, 2 ml isopropanol and 0.101 ml of 5% NAFION solution; the $IrO_2$ ink is then hand-painted onto a 5% wet proofed carbon fiber paper covering an area of 6 cm×6 cm; then, it is sintered at 80° C. for 30 minutes;
   (c) an anion-conducting polymeric membrane interposed between the inked sides of said cathode and said anode to form a membrane electrode assembly, said membrane electrode assembly mounted in a fuel cell hardware assembly with serpentine reactant flow field channels, said membrane meeting the following test:
   when (i) $CO_2$ humidified at 65° C. is fed into the cathode at a rate of 20 sccm and 10 mM $KHCO_3$ is fed into the anode flow field at a flow rate of 3 ml/min, (ii) the cell is heated to 50° C., (iii) a power supply interconnects said cathode and said anode, (iv) the cell is maintained at 3 V for 2 hours, and then switched to constant current mode at 200 $mA/cm^2$; (v) the cell is maintained in constant current mode for at least 100 hours, (vi) selectivity is calculated as follows:

$$\text{Selectivity} = \frac{(\text{CO production rate})}{(\text{CO production rate} + H_2 \text{ production rate})}$$

and (vii) CO and $H_2$ production rates are measured in standard cubic centimeters per minute exiting the cell, selectivity is greater than 90%, and the voltage to maintain 200 $mA/cm^2$ is less than 3 V.

* * * * *